United States Patent [19]

Yoshida

[11] Patent Number: Plant 5,595

[45] Date of Patent: Dec. 10, 1985

[54] AFRICAN VIOLET (LYNN)

[76] Inventor: Eiichi Yoshida, P.O. Box 4836, Hayward, Calif. 94540

[21] Appl. No.: 579,176

[22] Filed: Feb. 10, 1984

[51] Int. Cl.[4] ..... A01H 5/00

[52] U.S. Cl. ..... Plt./69

[58] Field of Search ..... Plt./69

*Primary Examiner*—Robert E. Bagwill

[57] ABSTRACT

A new variety of African violet plant for potted plant culture particularly distinguished by its year around blooming capability, its profuse production of bi-colored flowers, and its compact, girl-leaf foliage of dark green color. An ideal plant for small potted plant production.

1 Drawing Figure

BACKGROUND OF THE NEW PLANT

To obtain this new variety of African violet plant, the inventor cross-pollenated the seed parent "Rhapsodie" Maria Saintpaulia and the pollen parent "Rhapsodie" Denise Saintpaulia. The seed pods of the pollenated plants were used as the generic basis for initiating further experimental series. Approximately 25 seedlings were selected by very rigid standards for further propagation. Propagation of these plants and refinement out of limited selected plants continued and tests were conducted for the development of permanent characteristics of disease resistance, early blooming and vigorous growth.

The descendants of the original plants were completely the same in appearance as the parent plant.

DESCRIPTION OF THE PLANT

Sheet one is a full color photographic view of the plant in bloom, the colors shown being as nearly true as it is reasonably possible to obtain by conventional photographic procedures.

The following is a detailed description of my new African violet plant with the color designation being accorded to The R.H.S. Colour Chart published by The Royal Horticultural Society of London, England, with collaboration by the British Colour Council.

THE PLANT

Origin: Seedling, #H-210/2.

Parentage:

*Seed parent.*—"Rhapsodie" Maria.

*Pollen parent.*—"Rhapsodie" Denise.

Classification:

*Botanic.*—Saintpaulia Ionanthe.

*Commercial.*—African Violet.

Form: Rosette arrangement.

Height: 11.5 to 13.7 cm. tall.

Growth: New growth is vigorous and has a tendency to grow slightly upwards. As leaves get older they grow more horizontally and eventually grow somewhat downward.

Size: Small; overall plant diameter is from 16 to 19.2 cm.

Mutation prone: Very little for foliage. Occasionally, solid purple-violet colored flowers are produced by a plant.

Leaves: Brittle, girl type; slightly undulated.

*Shape.*—Ovate with slight crenate margins.

*Length.*—Approximately 6.7 cm. for a mature leaf.

*Width.*—Approximately 6.4 cm. for a mature leaf.

*Color.*—Upperside: Medium green, light green at petiole. Underside: Light green.

*Texture.*—Upperside; Pubescent. Underside: Pubescent.

*Ribs and veins.*—Pinnate, slightly sunken on leaf surface, pronounced on underside of leaf.

*Petiole.*—Round, a small section on top is flattened along its length. Light green. Pubescent on top, puberulent on its underside. Length varies with age of leaf and plant.

THE FLOWER

Blooming habit: Continuous and abundant under optimum growing conditions.

Number: Five to nine per peduncle.

Size of flower: Each flower is from 3.8 to 4.2 cm. in diameter.

Color: The flower is White Group, 155-C; center eye and margin is Purple-Violet Group, 82-A, from The R.H.S. Colour Chart.

Type: Single.

Petals: Five per individual flower, smooth margins.

Texture: Smooth and flexible.

Appearance: Guttery upper surface. Underside is shiny with small bumps and is puberulent.

Peduncles: Short, strong, light green, and pubescent.

Inflorescence: Cyme, upright, above foliage.

Calyx: Quinquepartite, light green, puberulent.

Persistence: Flowers do not drop. Old flowers dry up on stem.

Fragrance: None.

REPRODUCTIVE ORGANS

Stamens: Usually two per flower and joined at top of anthers.

*Anthers.*—Visible, bright yellow, fade slightly as they get older; one on each filament.

*Filaments.*—Approximately 0.3 cm. long.

*Pollen.*—Light yellow, ripens before stigma.

Pistils: Normally one per flower.

*Stigma.*—Usually visible and accessible. When receptive, it becomes swollen and usually exudes a small drop of clear fluid.

*Style.*—Approximately 0.7 cm. long.

*Ovary.*—Superior.

OTHER CHARACTERISTICS

This variety of African violet is very suited for small potted plant culture and its year around blooming capability gives the plant a commercially attractive value.

I claim:

1. An African Violet plant substantially as shown and described.

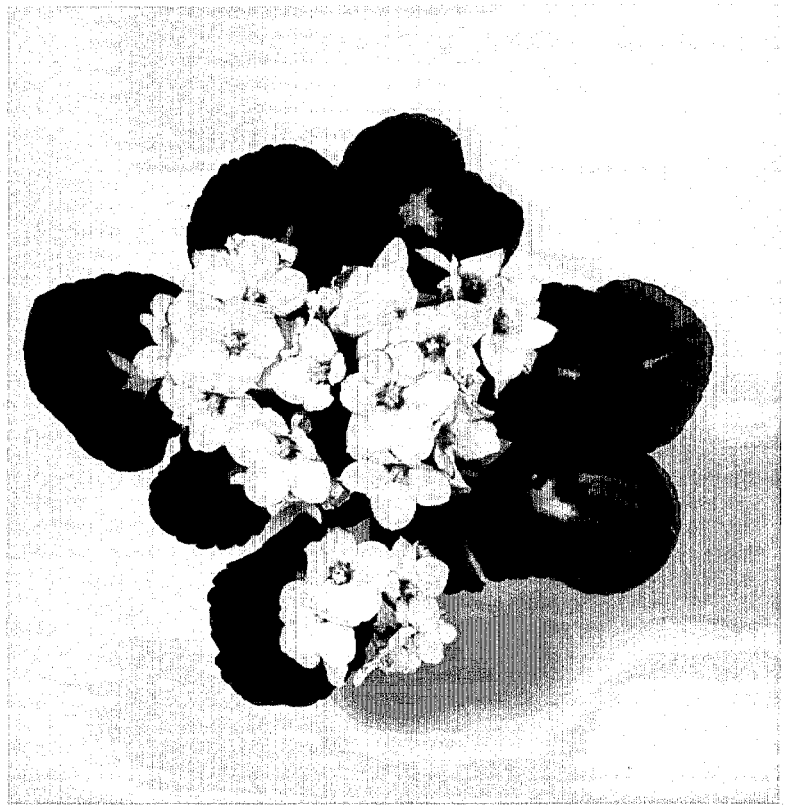

* * * * *